(12) United States Patent
Hopkinson et al.

(10) Patent No.: US 8,563,471 B2
(45) Date of Patent: Oct. 22, 2013

(54) SUBMICRON MESOTRIONE COMPOSITIONS

(75) Inventors: Michael Hopkinson, Greensboro, NC (US); Giulia Capuzzi, Greensboro, NC (US); Sarah Cush, Greensboro, NC (US); Carolyn Moore, Greensboro, NC (US)

(73) Assignee: Syngenta Crop Protection LLC, Greensboro, NC (US)

( * ) Notice: Subject to any disclaimer, the term of this patent is extended or adjusted under 35 U.S.C. 154(b) by 148 days.

(21) Appl. No.: 10/580,063

(22) PCT Filed: Nov. 30, 2004

(86) PCT No.: PCT/US2004/039929
§ 371 (c)(1),
(2), (4) Date: Jan. 9, 2007

(87) PCT Pub. No.: WO2005/055714
PCT Pub. Date: Jun. 23, 2005

(65) Prior Publication Data
US 2007/0225169 A1    Sep. 27, 2007

Related U.S. Application Data

(60) Provisional application No. 60/527,364, filed on Dec. 5, 2003.

(51) Int. Cl.
*A01N 63/00*    (2006.01)
*A01N 35/00*    (2006.01)
*A01N 63/02*    (2006.01)

(52) U.S. Cl.
USPC .......................... 504/118; 504/348; 977/902

(58) Field of Classification Search
USPC .................................. 504/118, 348; 977/902
See application file for complete search history.

(56) References Cited

U.S. PATENT DOCUMENTS

| | | | | |
|---|---|---|---|---|
| 5,912,207 | A  * | 6/1999 | Scher et al. | 504/190 |
| 6,746,988 | B2 * | 6/2004 | Hopkinson et al. | 504/127 |
| 6,924,250 | B2 * | 8/2005 | Cornes | 504/136 |
| 2003/0148887 | A1 | 8/2003 | Bratz et al. | |
| 2003/0186816 | A1* | 10/2003 | Hacker et al. | 504/134 |
| 2005/0233907 | A1* | 10/2005 | Nabors et al. | 504/149 |
| 2007/0122436 | A1* | 5/2007 | Koltzenburg et al. | 424/405 |

OTHER PUBLICATIONS

Dyson et al. "Journal of Environmental Quality, 31:613-618 (2002).*

* cited by examiner

*Primary Examiner* — Fereydoun G Sajjadi
*Assistant Examiner* — Courtney Brown
(74) *Attorney, Agent, or Firm* — James Cueva

(57) ABSTRACT

The present invention relates to novel suspension concentrate and suspoemulsion formulations comprising a herbicidally active amount of 2-(2'-nitro-4'-methylsulphonylbenzoyl)-1,3-cyclohexanedione(mesotrione), as well as agrochemically acceptable salts thereof, having a particle size, as defined herein, of less than 1 micron and to the use of thereof in controlling weeds in crops of useful plants.

32 Claims, No Drawings

SUBMICRON MESOTRIONE COMPOSITIONS

The present invention relates to novel suspension concentrate and suspoemulsion formulations comprising a herbicidally active amount of 2-2'-nitro-4'-methylsulphonylbenzoyl)-1,3-cyclohexanedione (mesotrione), as well as agrochemically acceptable salts thereof, having an average particle size, as defined herein, of less than 1 micron.

The present invention also relates to herbicidal compositions for controlling grasses and weeds in crops of useful plants, especially in crops of maize and cereals, prepared from these suspension concentrate and suspoemulsion formulations, and to the use of such compositions in controlling weeds in crops of useful plants.

BACKGROUND OF THE INVENTION

Crop protection agents are often administered in the form of aqueous systems. Water-based formulations are obtained by dissolving, emulsifying and/or suspending pesticide technical materials in water. The efficient use of aqueous systems with certain crop protection agents, however, may be restricted due to their poor water-solubility. Aqueous systems containing solid pesticide technical materials may be formulated as suspension concentrates or suspoemulsion formulations. However, these formulation types can suffer from a variety of problems such as agglomeration of solid particles, irreversible thickening, serum formation or sedimentation of solids as a hard packed precipitate. In the case of suspoemulsions, the presence of an emulsified oil layer increases the risk of formulation failure due to the intrinsic instability of oil-in-water emulsions. Due to the relatively complex supply chain for crop protection agents, the formulations can be stored for long periods and may be subjected during storage and shipping to extreme temperature variations, high-shear and repetitive vibration patterns which can increase the likelihood of failure.

SUMMARY OF THE INVENTION

It is an object of the present invention to prepare aqueous systems comprising mesotrione that exhibit improved physical storage stability, handling and dilution characteristics compared to a similarly formulated mesotrione composition containing mesotrione having an average particle size in excess of 1 micron.

The present invention relates to novel suspension concentrate and suspoemulsion formulations comprising a herbicidally active amount of 2-(2'-nitro-4'-methylsulphonylbenzoyl)-1,3-cyclohexanedione (mesotrione), as well as agrochemically acceptable salts thereof, having an average particle size, as defined herein, of less than 1 micron, preferably less than 800 nanometers (nm).

The present invention also relates to herbicidal compositions for controlling grasses and weeds in crops of useful plants, especially in crops of maize and cereals, prepared from these suspension concentrate and suspoemulsion formulations, and to the use of such compositions in controlling weeds in crops of useful plants.

One embodiment of the invention relates also to suspension concentrates comprising mesotrione having an average particle size of less than 1 micron, preferably less than 800 nm, and a dispersing agent.

In another embodiment, the invention relates to a suspoemulsion formulation comprising:
(A) a continuous aqueous phase;
(B) (i) a dispersed emulsion phase comprising at least one liquid, water-insoluble active ingredient;
(ii) an emulsifier in an amount sufficient to emulsify the liquid, water-insoluble ingredients; and
(C) (i) mesotrione having an average particle size of less than 1 micron, preferably less than 800 nm, as a dispersed solid phase;
(ii) a dispersing agent in an amount sufficient to disperse the mesotrione as well as any other solid technical materials present in the formulation;
wherein the solid phase is dispersed in said aqueous and/or emulsion phase.

DETAILED DESCRIPTION OF THE INVENTION

The term "mesotrione" herein means 2-(2'-nitro-4'-methylsulphonyl benzoyl)-1,3-cyclohexanedione including any enolic tautomeric forms that may give rise to geometric isomers. Furthermore, in certain cases, the various substituents may contribute to optical isomerism and/or stereoisomerism. All such tautomeric forms, racemic mixtures and isomers are included within the scope of the present invention. Unless otherwise specified, the term "mesotrione" includes the agriculturally acceptable salts of 2-(2'-nitro-4'-methylsulphonyl benzoyl)-1,3-cyclohexanedione as well.

Agriculturally acceptable salts for use in the present invention include salts the cations or anions of which are known and accepted in the art for the formation of salts for agricultural or horticultural use. Useful salts for practice of the invention may be formed from 2-(2'-nitro-4'-methylsulphonyl benzoyl)-1,3-cyclohexanedione using amines, alkali metal bases, alkaline earth metal bases, quaternary ammonium bases, and metal chelates. Also included are metal chelates of 2-(2'-nitro-4'-methylsulphonyl benzoyl)-1,3-cyclohexanedione including salts of di- and trivalent transition metal ions such as $Cu^{+2}$, $Zn^{+2}$, $Co^{+2}$, $Ni^{+2}$, $Ca^{+2}$, $Al^{+3}$, $Ti^{+3}$, $Fe^{+2}$, $Fe^{+3}$, $Ba^{+2}$, $Cs^{+2}$, and also $[CH_3(CH_2)_7]3N$.

Examples of suitable amines for ammonium salt formation that come into consideration are ammonia as well as primary, secondary and tertiary $C_{1-18}$ alkylamines, $C_{1-4}$ hydroxyalkylamines and $C_{2-4}$ alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimnethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary aryl amines for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Metal chelates of 2-(2'-nitro-4'-methylsulphonyl benzoyl)-1,3-cyclohexanedione and their preparation are described, inter alia, in PCT Publication No. WO97/27748. The preferred metal ions are divalent transition metal ions, particularly $Cu^{+2}$, $Co^{+2}$, $Ni^{+2}$, and $Zn^{+2}$; with $Cu^{+2}$ being especially preferred. Any appropriate salt which would be a source of a di- or trivalent metal ion may be used to form the metal chelate of the dione compound in accordance with this invention. Particularly suitable salts include: chlorides, sulphates, nitrates, carbonates, phosphates and acetates. In a preferred embodiment of the present invention, the mesotrione is in the form of a metal chelate of mesotrione, preferably a copper or zinc chelate of mesotrione.

Due to the limitations of different measuring techniques and in order to more accurately characterize the mesotrione particle size, the mesotrione is characterized by two different techniques for measuring the particle size. As used herein, the phrase "mesotrione having an average particle size of less than 1 micron, preferably less than 800 nm" refers to mesotrione compositions wherein the average particle size as determined by both Dv50 and Z-average is below 1 micron, preferably less than 800 nm. The Dv50 and Z-average will be similar when the particle size distribution is narrow and below 1 micron. They will not be similar when there is a significant fraction of particles larger than 1 micron. The Z-average diameter of the mesotrione particles as defined herein is measured by photon correlation spectroscopy using equipment readily determinable by those ski led in the art such as a Malvern Nanosizer. The Dv50 particle size of the mesotrione particles is the median particle size as determined using available analytical devices such as a Malvern Mastersizer.

The invention relates also to aqueous suspension concentrates comprising a herbicidally effective amount of mesotrione having an average particle size of less than 1 micron, preferably less than 800 nm, and a dispersing agent.

Another embodiment of the present invention relates to a suspoemulsion formulation comprising:
(A) a continuous aqueous phase;
(B) (i) a dispersed emulsion phase comprising at least one liquid, water-insoluble active ingredient;
    (ii) an emulsifier in an amount sufficient to emulsify the liquid, water-insoluble active ingredients; and
(C) (i) a herbicidally effective amount of mesotrione having an average particle size of less than 1 micron, preferably less than 800 nm, as a dispersed solid phase;
    (iii) a dispersing agent in an amount sufficient to disperse the mesotrione as well as any other solid technical materials present in the formulation;
wherein the solid phase is dispersed in said aqueous and/or emulsion phase.

The suspoemulsion formulation of the present invention may optionally further comprise one or more additional active ingredients. The one or more additional active ingredients may be a pesticide, for example a herbicide, fungicide, insecticide or the like; or the additional active ingredient may be a compound selected from the class of compounds known as safeners or antidotes. The concentration of additional active ingredient in the formulation is suitably in the range of from 1 g/l to 500 g/l, and preferably from 2 g/l to 300 g/l.

In one embodiment, the liquid, water-insoluble active ingredient comprises at least one member selected from the group consisting of acetamide herbicides and safeners or antidotes.

Preferred liquid, water-insoluble active ingredients include acetamide herbicides and safeners. Representative acetamide herbicides include diphenamid, napropamide, naproanilide, acetochlor, alachlor, butachlor, dimethachlor, dimethenamid, dimethenamid-P, fentrazamide, metazachlor, metolachlor, pethoxamid, pretilachlor, propachlor, propisochlor, S-metolachlor, thenylchlor, flufenacet and mefenacet. Where the acetamide herbicide is liquid at ambient temperatures, i.e., has a melting point below about 0° C., the oil phase can consist essentially or substantially of the acetamide herbicide itself. In other words, no organic solvent is necessary, although one can optionally be included. Examples of acetamide herbicides that are liquid at ambient temperatures and can be formulated in compositions of the invention without the need for an organic solvent include acetochlor, butachlor, metolachlor, S-metolachlor and pretilachlor. Where an organic solvent is desired or required, any suitable organic solvent known in the agricultural chemical formulating art in which the acetamide herbicide is adequately soluble can be used. Preferably the organic solvent is one in which the acetamide herbicide is highly soluble, so that as high as possible a concentration of the acetamide herbicide can be accommodated in the oil phase and in the composition as a whole.

As used herein, the term acetamide includes mixtures of the two or more acetamides as well as mixtures of optical isomers of the acetamides. For example, mixtures of the (R) and (S) isomers of metolachlor wherein the ratio of (S)-2-chloro-N-(2-ethyl-6-methylphenyl)-N-(2-methoxy-1-methylethyl)acetamide to (R)-2-chloro-N-(2-ethyl-6-methylphenyl)-N-(2-methoxy-1-methylethyl)acetamide is in the range of from 50-100% to 50-0%, preferably 70-100% to 30-0% and more preferably 80-100% to 20-0% are included.

Preferred acetamides include mixtures of metolachlor (S) and (R) isomers wherein the ratio of (S)-2-chloro-N-(2-ethyl-6-methylphenyl)-N-(2-methoxy-1-methylethyl)acetamide to (R)-2-chloro-N-(2-ethyl-6-methylphenyl)-N-(2-methoxy-1-methylethyl)acetamide is in the range of from 50-100% to 50-0%, preferably 70-100% to 30-0% and more preferably 80-100% to 20-0%.

Safeners suitable for use in the present invention include benoxacor; cloquintocet; cloquintocet-mexyl; dichlormid; fenchlorazole-ethyl; fenclorim; flurazole; fluxofenim; furilazole; isoxadifen-ethyl; mefenpyr; an alkali metal, alkaline earth metal, sulfonium or ammonium cation of mefenpyr; mefenpyr-diethyl and oxabetrinil. Preferred safeners include benoxacor and dichlormid. When a liquid acetamide is used the safener will generally be dissolved in the acetamide phase. However, an organic solvent can optionally be used. Where an organic solvent is desired or required, any suitable organic solvent known in the agricultural chemical formulating art in which the acetamide herbicide and safener are adequately soluble can be used. Preferably the organic solvent is one in which the acetamide herbicide and safener are highly soluble, so that as high as possible a concentration of the active components can be accommodated in the oil phase and in the composition as a whole.

The suspension concentrates and suspoemulsion formulations of the present invention may contain, in addition to mesotrione, at least one solid, water-insoluble active ingredient. Suitable solid, water-insoluble active ingredients for use in the present invention include glyphosate acid, triazine herbicides, for example, atrazine, simazine or terbuthylazine, isoxazole herbicides such as isoxaflutole and sulfonylurea herbicides such as primisulfuron, prosulfuron or nicosulfuron.

The suspension concentrates and suspoemulsion formulations may further comprise additional active ingredients that are soluble in the aqueous phase. Water-soluble active ingredients include pesticides or plant growth regulators such as acephate, acifluorfen, acrolein, amitrole, asulam, benazolin, bentazon, bialaphos, borax, bromacil, bromoxynil, butoxycarboxim, calcium polysulfide, cartap, chloramben, chlormequat, chloroacetic acid, chlorphonium, clofencet, clopyralid, cloxyfonac, copper sulfate, cyanamide, 2,4-D, 2,4-DB, dalapon, daminozide, dicamba, dichlorprop, diclofop, dicrotophos, difenzoquat, dikegulac, diquat, endothall, ethephon, fenac, fenoxaprop, flamprop, fluazifop, fluoroglycofen, flupropanate, fomesafen, formetanate, fosamine, fosetyl, glufosinate, glyphosate, guazatine, haloxyfop, hydroxyquinoline sulfate, imazameth, imazamethabenz, imazamox, imazapic, imazapyr, imazaquin, imazethapyr, iminoctadine, ioxynil, kasugamycin, MCPA, MCPB, mecoprop, mepiquat, mercuric chloride, metam, methamidophos, methomyl, methylarsonic acid, mevinphos, monocrotophos, nabam, naptalam, nicotine, nitenpyram, nonanoic acid, omethoate, oxamyl, oxydemeton-methyl, paraquat, phosphamidon, picloram, polyoxin B, propamocarb, sulfamic acid, 2,3,6-TBA, thiocyclam, trichlorfon, trichloroacetic acid, triclopyr, validamycin and vamidothion, as well as agriculturally acceptable salts and esters thereof. Preferred water-soluble active ingredients include glyphosate or salts thereof and glufosinate or salts thereof.

As used herein, the term "herbicidally effective amount" means the amount of herbicide compound which adversely controls or modifies plant growth. Controlling or modifying effects include all deviation from natural development, for example, killing, retardation, leaf burn, albinism, dwarfing and the like. The term plants refers to all physical parts of a plant, including seeds, seedlings, saplings, roots, tubers, stems, stalks, foliage and fruits.

The surfactant system allowing the water-insoluble solids to be dispersed in the aqueous phase and the liquid technical materials (active ingredients) to be emulsified in the continuous water phase is typically a mixture of two or more surfactants, at least one of which is a nonionic surfactant and optionally at least one of which is an anionic surfactant.

In a suspoemulsion formulation surfactants function as emulsifiers to emulsify oily liquid technical materials and dispersants to disperse solid water-insoluble technical materials. These surfactants should be compatible in one formulation. A surface-active agent may act as both an emulsifier and a dispersant.

Suitable surface-active compounds are, depending on the nature of the active ingredient, non-ionic, cationic and/or anionic surfactants and mixtures of surfactants having good emulsifying, dispersing and wetting properties. Examples of suitable anionic, non-ionic and cationic surfactants are listed, for example, in U.S. Pat. No. 6,063,732 column 5, line 1 to column 6, line 2, the contents of which are incorporated herein by reference.

Furthermore, the surfactants customarily employed in formulation technology, which are described, inter alia, in "Mc Cutcheon's Detergents and Emulsifiers Annual" MC Publishing Corp., Ridgewood N.J., 1981, Stache, H., "Tensid-Taschenbuch", Carl Hanser Verlag, MunichNienna, 1981 and M. and J. Ash, "Encyclopedia of Surfactants", Vol I-III, Chemical Publishing Co., New York, 1980-81, are also suitable for preparation of the herbicidal compositions according to the invention.

Anionic surfactants suitable for use in the invention may be any known in the art. The anionic surfactants may be polyarylphenol polyalkoxyether sulfates and/or phosphates; $C_{8-18}$ alcohol polyalkoxyether phosphates, carboxylates, and/or citrates; alkyl benzenesulfonic acids; $C_{8-20}$ alkyl catboxylates including fatty acids; $C_{8-20}$ alcohol sulfates; $C_{8-20}$ alcohol phosphate mono- and diesters; $C_{8-20}$ alcohol and ($C_{8-20}$ alkyl)phenol polyoxyethylene ether carboxylates, sulfates and sulfonates; $C_{8-20}$ alcohol and ($C_{8-20}$ alkyl)phenol polyoxyethylene phosphate mono- and diesters; $C_{8-20}$ alkylbenzene sulfonates, naphthalene sulfonates and formaldehyde condensates thereof; lignosulfonates; $C_{8-20}$ alkyl sulfosuccinates and sulfosuccinamates; $C_{8-20}$ acyl glutamates, sarcosinates, isethionates and taurates; water-soluble soaps and mixtures thereof.

Exemplary polyarylphenol polyalkoxyether sulfates and phosphates include polyarylphenol polyethoxyether sulfates and phosphates, polyarylphenol polypropoxyether sulfates and phosphates, polyarylphenol poly(ethoxy/propoxy)ether sulfates and phosphates, and salts thereof. The term "aryl" includes, for example, phenyl, tolyl, naphthyl, tetrahydronaphthyl, indanyl, indenyl, styryl, pyridyl, quinolinyl, and mixtures thereof Exemplary polyarylphenol polyethoxyether sulfates and phosphates include distyrylphenol polyethoxyether sulfates and phosphates, and tristyrylphenol polyethoxyether sulfates and phosphates. The polyarylphenol polyalkoxether sulfates and phosphates may have a degree of alkoxylation (e.g., ethoxylation) of between about 1 and about 50, preferably between about 2 and about 40, more preferably between about 5 and about 30. Commercially available polyarylphenol polyalkoxyether sulfates and phosphates include, for example, SOPROPHOR® 4 D 384 (Rhodia Corporation, Cranbury, N.J.) (tristyrylphenol $(EO)_{16}$ sulfate ammonium salt), SOPROPHOR® 3 D 33 (Rhodia Corporation, Cranbury, N.J.) (tristyrylphenol (EO)16 phosphate free acid), SOPROPHOR® FLK (Rhodia Corporation, Cranbury, N.J.) (tristyrylphenol (EO)16 phosphate potassium salt) and SOPROPHOR® RAM/384 (Rhodia Corporation, Cranbury, N.J.) (tristyrylphenol polyethoxylated ether sulfate neutralized with polyethoxylated oleylamine). In other embodiments, the polyarylphenol polyalkoxy ether sulfates and phosphates may be mono-arylphenol polyalkoxyether sulfates and phosphates, such as styrylphenol polyethoxyether sulfates and phosphates.

Exemplary $C_{8-18}$ alcohol polyethoxyether phosphates, carboxylates and citrates include STEPFAC® 8180 (Stepan Corporation, Northfield, Ill.) (tridecylalcohol $(EO)_3$ phosphate), STEPFAC® 8181 (Stepan Corporation, North field, Ill.) (tridecylalcohol $(EO)_6$ phosphate), STEPFAC® 8182 (Stepan Corporation, Northfield, Ill.) (tridecylalcohol $EO)_{12}$ phosphate), EMCOL® CN-6 (CK Witco Corporation, Greenwich, Conn.) (tridecylalcohol $EO)_6$ carboxylate). The $C_{8-18}$ alcohol polyethoxyether phosphates, carboxylates and citrates may have a degree of ethoxylation of between about 1 and about 25, preferably between about 1 and about 20.

Exemplary alkylbenzene sulfonic acids and salts thereof include dodecylbenzene sulfonic acid, and metal (for example sodium or calcium), ammonia or amine salts of the alkylbenzene sulfonic acids, including dodecylbenzene sulfonic acid. Amine neutralized versions include primary amines, diamines, triamines and alkanol amines.

Additional preferred anionic surfactants include ($C_{8-12}$ alkyl)phenol polyoxyethylene ether sulfates, and ($C_{8-12}$ alkyl)phenol polyoxyethylene phosphate mono- and diesters, accompanied in each case by monovalent counterions. In one embodiment the monovalent counterion for a ($C_{8-12}$ alkyl) phenol polyoxyethylene ether sulfate or a ($C_{8-12}$ alkyl)phenol polyoxyethylene phosphate is a protonated polyoxyethylene $C_{12-20}$ alkylamine surfactant. More specifically, polyoxyethylene tallowamine salt of a nonylphenol polyoxyethylene ether sulfate, nonylphenol polyoxyethylene phosphate, and a blend of such nonylphenol polyoxyethylene phosphate with polyoxyethylene tallowamine.

Suitable water-soluble soaps are the alkali metal salts, alkaline earth metal salts, ammonium salts or substituted ammonium salts of higher fatty acids ($C_{10}$-$C_{22}$), e.g. the sodium or potassium salts of oleic or stearic acid, or of natural fatty acid mixtures which can be obtained, inter alia, from coconut oil or tallow oil. Further suitable soaps are also the fatty acid methyl taurin salts.

The anionic surfactants are optionally neutralized with a basic compound. The basic compounds may be any known in the art that are capable of neutralizing the anionic surfactants. Basic compounds include, for example, inorganic bases, $C_{8-18}$ alkyl amine polyalkoxylates, alkanol amines, alkanol amides, and mixtures thereof.

Exemplary inorganic bases include ammonium hydroxides, sodium hydroxides, potassium hydroxides, calcium hydroxides, magnesium hydroxides, zinc hydroxides, and mixtures thereof. The $C_{8-18}$ alkyl amine polyalkoxylates may be, for example, $C_{8-18}$ alkyl amine polypropoxylates and/or $C_{8-18}$ alkyl amine polyethoxylates. Exemplary $C_{8-18}$ alkyl amine polyalkoxylates include tallow amine polyalkoxylates, cocoamine polyalkoxylates, oleylamine polyalkoxylates, and stearylamine polyalkoxylates. The $C_{8-18}$ alkyl amine polyethoxyates may have from about 2 to about 50 moles of ethylene oxide per molecule, more preferably from about 2 to about 20 moles of ethylene oxide per molecule. Exemplary $C_{8-18}$ alkyl amine polyethoxylates include tallow amine ethoxylates (2 moles EO or 8 moles EO), cocoamine ethoxylates, oleylamine ethoxylates, and stearylamine ethoxylates. Exemplary alkanol amines include diethanol amine and triethanol amine. Exemplary alkanol amides include oleic diethanolamide and linoleic diethanolamide, and the diethanolamides of other $C_{8-18}$ fatty acids.

For example, the compositions of the invention may comprise at least one polyarylphenol polyalkoxyether sulfate, polyarylphenol polyalkoxyether phosphate, $C_{8-18}$ alcohol polyalkoxyether phosphates, $C_{8-18}$ alcohol polyalkoxyether carboxylates, $C_{8-18}$ alcohol polyalkoxyether citrates, and/or alkyl benzenesulfonic acids.

In still other embodiments, the compositions of the invention comprise mixtures of at least two anionic surfactants selected from polyarylphenol polyalkoxyether sulfates, polyarylphenol polyalkoxyether phosphates, $C_{8-20}$ alkyl carboxylates including fatty acids, $C_{8-20}$ alcohol sulfates, $C_{8-20}$ alcohol phosphate mono- and diesters, $C_{8-20}$ alcohol and $(C_{8-20}$ alkyl)phenol polyoxyethylene ether carboxylates, sulfates and sulfonates, $C_{8-20}$ alcohol and $(C_{8-20}$ alkyl)phenol polyoxyethylene phosphate mono- and diesters, $C_{8-20}$ alkylbenzene sulfonates, naphthalene sulfonates and formaldehyde condensates thereof, lignosulfonates, $C_{8-20}$ alkyl sulfosuccinates and sulfosuccinamates, and/or $C_{8-20}$ acyl glutamates, sarcosinates, isethionates and taurates.

Exemplary nonionic surfactants include ethylene oxide-propylene oxide block copolymers; ethylene oxide-butylene oxide block copolymers; $C_{2-6}$ alkyl adducts of ethylene oxide-propylene oxide block copolymers; $C_{2-6}$ alkyl adducts of ethylene oxide-butylene oxide block copolymers; polypropylene glycols; polyethylene glycols; polyarylphenol polyethoxy ethers; polyalkylphenol polyethoxy ethers; polyglycol ether derivatives of aliphatic or cycloaliphatic alcohols or of saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols; mono-, di- and tri($C_{12-20}$ alkyl)esters of polyoxyethylene sorbitan; alkoxylated vegetable oils; alkoxylated acetylenic diols; alkyl polyglycosides and mixtures thereof.

The ethylene oxide-propylene oxide block copolymers may comprise alkyl or alkyphenol ether bases, such as butyl ether, methyl ether, propyl ether, ethyl ether, or mixtures thereof. Commercially available nonionic surfactants include, for example, TOXIMUL® 8320 (Stepan Corporation, Northfield, Ill.) (butyl ether derivative of EO/PO block copolymer), WITCONOL® NS-500LQ (CK Witco Corporation, Greenwich, Conn.) (butyl ether derivative of EO/PO block copolymer) and WITCONOL® NS-108LQ (CK Witco Corporation, Greenwich, Conn.) (nonylphenol ether derivative of EO/PO block copolymer).

Other suitable non-ionic surfactants are the water-soluble, 20 to 250 ethylene glycol ether groups containing polyadducts of ethylene oxide and propylene oxide, ethylene diamino polypropylene glycol and alkyl polypropylene glycol with 1 to 10 carbon atoms in the alkyl moiety, the substances normally contain 1 to 5 ethylene glycol units per propylene glycol unit. Examples of non-ionic surfactants are nonylphenol polyethoxy ethanols, vegetable oil polyglycol ethers, polyadducts of ethylene oxide and propylene oxide, tributyl phenoxy polyethoxy ethanol, octyl phenoxy polyethoxy ethanol. Preferred are fatty acid esters of polyoxy ethylene sorbitan, such as polyoxy ethylene sorbitan trioleate.

Alkyl polyglycosides known in the art can be used in the invention. The alkyl polyglycoside of the invention may have formula (I):

$$R_1O(R_2O)_b(Z)_a \qquad (I)$$

$R_1$ is a monovalent organic radical having from about 6 to about 30 carbon atoms. $R_1$ is preferably a $C_{8-22}$ alkyl or alkenyl group, more preferably a $C_{8-11}$ alkyl group. $R_2$ is a divalent alkylene radical having from about 2 to about 4 carbon atoms. $R_2$ is preferably ethylene or propylene, more preferably ethylene. b is 0 to about 100. b is preferably 0 to about 12, more preferably 0. Z is a saccharide residue having about 5 to about 6 carbon atoms. Z may be glucose, mannose, fructose, galasctose, talose, gulose, altrose, allose, apiose, gallose, idose, ribose, arabinose, xylose, lyxose, or a mixture thereof; Z is preferably glucose; 'a' is an integer from 1 to about 6, 'a' is preferably from 1 to about 3, more preferably about 2.

Preferred compounds of formula (I) are compounds of formula (II):

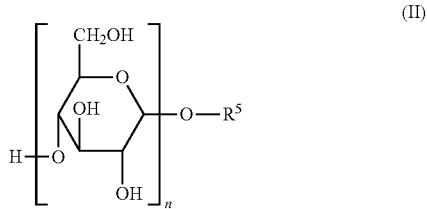

where n is the degree of polymerization and is from 1 to 3, preferably 1 or 2, and $R^5$ is a branched or straight chain alkyl group having from 4 to 18 carbon atoms or a mixture of alkyl groups having from 4 to 18 carbon atoms.

Exemplary alkyl polyglycosides include APG® 325 (Cognis Corporation, Cincinnati, Ohio) (an alkyl polyglycoside in which the alkyl group contains 9 to 11 carbon atoms and has an average degree of polymerization of 1.6), PLANTAREN® 2000 (Cognis Corporation, Cincinnati, Ohio) (an alkyl polyglycoside in which the alkyl group contains 8 to 16 carbon atoms and has an average degree of polymerization of 1.4), PLANTAREN® 1300 (Cognis Corporation, Cincinnati, Ohio) (an alkyl polyglycoside in which the alkyl group contains 12 to 16 carbon atoms and has an average degree of polymerization of 1.6), AGRIMUL® PG 2067 (Cognis Corporation, Cincinnati, Ohio) (an alkyl polyglycoside in which the alkyl group contains 8 to 10 carbon atoms and has an average degree of polymerization of 1.7), AGRIMUL® PG 2069 (Cognis Corporation, Cincinnati, Ohio) (an alkyl polyglycoside in which the alkyl group contains 9 to 11 carbon atoms and has an average degree of polymerization of 1.6), AGRIMUL® PG 2076 (Cognis Corporation, Cincinnati, Ohio) (an alkyl polyglycoside in which the alkyl group contains 8 to 10 carbon atoms and has an average degree of polymerization of 1.5), ATPLUS® 438 (Uniqema, Inc., Wilmington, Del.) (an alkylpolysaccharide in which the alkyl group contains 9 to 11 carbon atoms), and ATPLUS® 452 (Uniqema, Inc., Wilmington, Del.) (an alkylpolysaccharide in which the alkyl group contains 8 to 10 carbon atoms).

Cationic surfactants are preferably quaternary ammonium salts carrying, as N-substituent, at least one $C_8$-$C_{22}$ alkyl radical and, as further substituents, unsubstituted or halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl)ethylammonium bromide.

The amount of surfactant(s) depends on the particular active ingredients selected for the composition and the absolute and relative amounts of these desired. Suitable amounts of stabilizing system components selected from the classes or specific examples provided herein can be determined by routine experimentation, the test being that substantially no phase separation, sedimentation or flocculation is exhibited by the composition following storage at 20-25° C. for a period of 24 hours, or, for preferred embodiments, following a longer period of storage over a broader range of temperatures as indicated above. Typically the total concentration of all surfactants in the composition as a whole is about 1% to about 30% by weight, excluding the weight of counterions, if present.

In computing relative amounts of surfactants present in a composition, the weight of water or other diluent supplied with a surfactant, if known, should be excluded. For example, WITCONATE® 79S of CK Witco Corporation contains 52% dodecylbenzene sulfonic acid triethanolamine salt. In a composition containing 1% WITCONATE® 79S, the concentration of dodecylbenzene sulfonic acid triethanolamine salt should be computed as 0.52%.

These compositions may also comprise other auxiliaries such as wetting agents, chemical stabilizers, viscosity controlling agents, thickeners, binders, tackifiers, fertilizers and anti-foam agents.

Examples of suitable polymeric stabilizers that may be used in the present invention have a molecular weight between 10,000 and 1,000,000 daltons and include, but are not limited to polypropylene, polyisobutylene, polyisoprene, copolymers of monoolefins and diolefins, polyacrylates, polystyrene, polyvinyl acetate, polyurethanes or polyamides.

Examples of suitable stabilizing metal salts that may be used include calcium, beryllium, barium, titanium, magnesium, manganese, zinc, iron, cobalt, nickel and copper salts; most suitable are magnesium, manganese, zinc, iron, cobalt, nickel and copper salts; especially preferred is a copper salt, for example copper hydroxide.

Representative anti-foam agents are silica, polydialkylsiloxanes, in particular polydimethylsiloxanes, fluoroaliphatic esters or perfluoroalkylphosphonic/perfluoroalkylphosphonic acids or the salts thereof and mixtures thereof. Preferred are polydimethylsiloxanes.

The invention relates also to pesticide compositions obtained by i) diluting the suspension concentrate or suspoemulsion formulation of the present invention in a suitable carrier, such as water, such that the final concentration of the pesticide is between about 0.01% and about 10% of active ingredient (a.i.).

The invention relates also to a method for controlling undesired plant growth in crops of useful plants, said method comprising forming a pesticidal composition by i) diluting the suspension concentrate or suspoemulsion formulation of the present invention in a suitable carrier, such as water, such that the final concentration of the mesotrione is between about 0.01% and about 10% of active ingredient (a.i.) and ii) treating the desired area, such as crop, their seeds or seedlings or the crop area, with said composition.

The composition according to the invention is suitable for all methods of application conventionally used in agriculture, e.g. pre-emergence application, post-emergence application and seed dressing. The compositions according to the invention are preferably used for pre- or post-emergence control of weeds.

The compositions according to the invention are suitable especially for controlling weeds in crops of useful plants, preferably maize. "Crops" are to be understood also to include those crops that have been made tolerant to pests and pesticides, including herbicides or classes of herbicides, as a result of conventional methods of breeding or genetic engineering. The components used in the composition of the invention can be applied in a variety of ways known to those skilled in the art, at various concentrations. The rate at which the compositions are applied will depend upon the particular type of weed to be controlled, the degree of control required, and the timing and method of application. In general, the compositions can be applied in an amount such that the mesotrione is applied at a rate of 20-300 g a.i./ha, preferably 40-250 g a.i./ha.

Crop areas are areas of land on which the cultivated plants are already growing or in which the seeds of those cultivated plants have been sown, and also areas of land on which it is intended to grow those cultivated plants.

The weeds to be controlled may be either monocotyledonous or, preferably, dicotyledonous weeds, for example the monocotyledonous weeds *Avena, Agrostis, Phalaris, Lolium, Bromus, Alopecurus, Setaria, Digitaria, Brachiaria, Echinochloa, Panicum, Sorghum hal./bic., Rottboellia, Cyperus, Brachiaria, Echinochloa, Scirpus, Monochoria* and *Sagittaria* and the dicotyledonous weeds *Sinapis, Chenopodium, Stellaria, Galium, Viola, Veronica, Matricaria, Papaver, Solanum, Abutilon, Sida, Xanthium, Amaranthus, Ipomoea, Polygonum* and *Chrysanthemum.*

Other active ingredients such as co-herbicides, fungicides, insecticides, acaricides and nematicides may be present in the suspension concentrates or suspoemulsion formulations of the present invention or may be added as a tank-mix partner with the suspension concentrate or suspoemulsion formulation.

The following examples illustrate further some of the aspects of the invention but are not intended to limit its scope. Where not otherwise specified throughout this specification and claims, percentages are by weight.

Example 1

Re-Dispersing of Mesotrione Millbase

Stability protocol: The millbase, as described in section 3.2, is stored in 2 oz. jars at 38° C. for 6 weeks. The ability to re-disperse sediment is rated on how long, shaking at a moderate speed, it takes to homogenize the sample. Shorter times to re-disperse the sediment are desirable. Jars are shaken horizontally and one complete shake is noted as a complete forward and backward motion. Moderate shaking is approximately 2 complete shakes per second. The sediment must be completely re-dispersed, all sediment free from the bottom of the jar and no lumps or agglomerates in the bulk of the sample.

Sample 1-1 represents a submicron millbase as set forth in section 3.2. Sample 1-2 has a similar composition but contains millbase having larger particles.

TABLE 1

| Sample | Particle Size Malvern Nanosizer* (Z-average, μm) | Particle Size Malvern Mastersizer* (Median, Dv50, μm) | Time to Homogenize after 6 weeks at 38 C. |
|---|---|---|---|
| 1-1 | 0.613 | 0.6 | 25 seconds |
| 1-2* | 0.925 | 1.23 | 54 seconds |

*Millbase outside the scope of the claimed invention

It is clear from the data set forth in Table 1, that the mesotrione millbase having an average particle size within the scope of the present invention (Example 1-1) is significantly easier to re-disperse than the mesotrione millbase outside of the scope of the present invention as evidenced by the significantly less time taken to homogenize the submicron millbase.

Example 2

Improved Final Product Dilution Performance with Submicron Millbase

Dilution protocol: The Final Product formulation, as set forth in 3.3, are diluted using a typical use rate in water with a hardness of 50 ppm and 1000 ppm. The samples are diluted in a 100 ml graduated cylinder with a total volume of 100 ml (formulation plus water). The samples are then inverted through 10 complete inversions to fully mix the sample. The cylinder is left undisturbed at room temperature for 24 hours. After 24 hours, the number of inversions to completely re-disperse the sediment is noted. The lower the number of inversions required to completely re-disperse the sediment represents an improvement in the ability to re-disperse the Final Product.

Sample 2-1 represents a submicron millbase as described in section 3.2 having an average particle size as set forth above in Example 1-1. Sample 2-2 has a similar composition but contains millbase having a larger average particle size as set forth above in Example 1-2.

TABLE 2

| Sample | FinalProduct/Millbase | 50 ppm | 1000 ppm |
|---|---|---|---|
| 2-1 | Final product with submicron millbase | 12 inversions | 12 inversions |
| 2-2* | Final product with non-submicron millbase | 40 inversions | 40 inversions |

*Final Product outside the scope of the claimed invention

It is clear from the data set forth in Table 2, that the Final Product formulation prepared from the mesotrione millbase having an average particle size within the scope of the present invention (Example 2-1) was significantly easier to re-disperse than the formulations containing the mesotrione millbase outside of the scope of the present invention as evidenced by the significantly fewer inversions required to homogenize the Final Product.

Example 3

Sample Preparation 3.1 Preparation of S-metolachlor EW

The S-metolachlor EW was prepared according to the following composition:

| | % wt |
|---|---|
| S-metolachlor | 66.67 |
| A herbicidal antidote | 3.33 |
| Polystyrene | 3.68 |
| A block copolymer | 1.00 |
| Silicone antifoaming agent | 0.18 |
| Water | 25.12 |

The polystyrene and antidote were dissolved in the s-Metolachlor.

The block copolymer was dissolved in the aqueous phase and the antifoam was added. The two were combined in such a way as to form an emulsified organic phase with a particle size of 1-40 microns.

3.2 Preparation of Mesotrione Millbase

The mesotrione millbase was prepared according to the following composition:

| | % wt |
|---|---|
| Mesotrione | 30.00 |
| A non-ionic surfactant | 3.50 |
| Acetic acid (56%) | 11.01 |
| Copper hydroxide (100%) | 5.00 |
| Silicone antifoaming agent | 0.10 |
| Xanthan gum | 0.10 |
| Water | 50.29 |

The water, acetic acid, non-ionic surfactant and mesotrione were mixed together. Copper hydroxide was then added. The antifoaming agent and xanthan gum were added and mixed until uniform. If needed, the millbase was milled to the desired particle size.

3.3 Preparation of Final Product

The Final Product was prepared according to the following composition:

| | % wt |
|---|---|
| S-metolachlor EW | 55.20 |
| Mesotrione millbase | 12.25 |
| Propylene glycol | 5.00 |
| A non-ionic surfactant | 6.00 |
| A block copolymer surfactant | 5.00 |
| Xanthan gum | 0.16 |
| A preservative | 0.15 |
| Water | rest |

The s-metolachlor EW, propylene glycol, the non-ionic surfactant, the block copolymer and some of the water were blended together. The mesotrione millbase was added and blended. Next, the xanthan gum and preservative were added and blended until uniform. The formulation was assayed and trimmed with water as needed.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

We claim:

1. A suspension concentrate comprising
a herbicidally effective amount of mesotrione, as well as agrochemically acceptable salts thereof, having an average particle size of less than 1 micron, and a median particle size of less than 1 micron; and
a dispersing agent.

2. The suspension concentrate according to claim 1 wherein the mesotrione, or agriculturally acceptable salt thereof, has an average particle size of less than 800 nanometers.

3. The suspension concentrate according to claim 1 wherein the mesotrione comprises a metal chelate of mesotrione.

4. The suspension concentrate according to claim 3 wherein the metal chelate of mesotrione comprises at least one member selected from the group consisting of copper or zinc chelates of mesotrione.

5. The suspension concentrate according to claim 1 further comprising at least one additional solid, water-insoluble active ingredient.

6. The suspension concentrate according to claim 1 wherein the at least one additional solid, water-insoluble active ingredient comprises at least one member selected from the group consisting of triazine herbicides, isoxazole herbicides and sulfonylurea herbicides.

7. The suspension concentrate according to claim 6 wherein the at least one additional solid, water-insoluble active ingredient comprises a triazine herbicide.

8. The suspension concentrate according to claim 1 further comprising a water-soluble active ingredient dissolved in the aqueous phase.

9. The suspension concentrate according to claim 8 wherein the water-soluble active ingredient comprises at least one member selected from the group consisting of glyphosate, glufosinate and agriculturally acceptable salts thereof.

10. A pesticidal composition obtained by diluting a suspension concentrate according to claim 1 in water.

11. The pesticidal composition of claim 10 further comprising at least one member selected from the group consisting of co-herbicides, fungicides, insecticides, acaricides and nematicides.

12. A method for controlling undesired plant growth in crops of useful plants, said method comprising treating the useful plants, their seeds or seedlings or the crop area thereof with a pesticidal composition according to claim 10.

13. The method of claim 12 wherein the pesticidal composition is applied pre- or post-emergent.

14. The method of claim 12 wherein the crop of useful plants is maize.

15. A suspoemulsion formulation comprising
(A) a continuous aqueous phase;
(B) (i) a dispersed emulsion phase comprising at least one liquid, water-insoluble active ingredient;
(ii) an emulsifier in an amount sufficient to emulsify the liquid, water-insoluble active ingredient; and
(C) (i) a herbicidally effective amount of mesotrione having a particle size of less than 1 micron and a median particle size of less than 1 micron as a dispersed solid phase;
(ii) a dispersing agent in an amount sufficient to disperse the mesotrione as well as any other solid technical materials present in the formulation;
wherein the solid phase is dispersed in said aqueous and/or emulsion phase.

16. The suspoemulsion formulation according to claim 15 wherein the mesotrione, or agriculturally acceptable salt thereof, has an average particle size of less than 800 nanometers.

17. The suspoemulsion formulation according to claim 15 wherein the mesotrione comprises a metal chelate of mesotrione.

18. The suspoemulsion formulation according to claim 17 wherein the metal chelate of mesotrione comprises at least one member selected from the group consisting of copper or zinc chelates of mesotrione.

19. The suspoemulsion formulation according to claim 15 wherein the liquid, water-insoluble active ingredient comprises at least one member selected from the group consisting of acetamide herbicides and safeners.

20. The suspoemulsion formulation according to claim 19 wherein the liquid, water-insoluble active ingredient comprises acetamide herbicides.

21. The suspoemulsion formulation according to claim 20 wherein the acetamide comprises mixtures of metolachlor (S) and (R) isomers wherein the ratio of (S)-2-chloro-N-(2-ethyl-6-methylphenyl)-N-(2-methoxy-1-methylethyl)acetamide to (R)-2-chloro-N-(2-ethyl-6-methylphenyl)-N-(2-methoxy-1-methylethyl)acetamide is in the range of from 50-100% to 50-0%.

22. The suspoemulsion formulation according to claim 15 further comprising at least one safener.

23. The suspoemulsion formulation according to claim 22 wherein the safener comprises at least one member selected from the group consisting of benoxacor and dichlormid.

24. The suspoemulsion formulation according to claim 15 further comprising at least one additional solid, water-insoluble active ingredient.

25. The suspoemulsion formulation according to claim 24 wherein the at least one additional solid, water-insoluble active ingredient comprises at least one member selected from the group consisting of triazine herbicides, isoxazole herbicides and sulfonylurea herbicides.

26. The suspoemulsion formulation according to claim 15 further comprising a water-soluble active ingredient dissolved in the aqueous phase.

27. The suspoemulsion formulation according to claim 26 wherein the water-soluble active ingredient comprises at least one member selected from the group consisting of glyphosate, glufosinate and agriculturally acceptable salts thereof.

28. A pesticidal composition obtained by diluting a suspoemulsion formulation according to claim 15 in water.

29. The pesticidal composition of claim 28 further comprising at least one member selected from the group consisting of co-herbicides, fungicides, insecticides, acaricides and nematicides.

30. A method for controlling undesired plant growth in crops of useful plants, said method comprising treating the useful plants, their seeds or seedlings or the crop area thereof with a pesticidal composition according to claim 28.

31. The method of claim 30 wherein the pesticidal composition is applied pre- or post-emergent.

32. The method of claim 30 wherein the crop of useful plants is maize.

* * * * *